(12) United States Patent
Bohlin

(10) Patent No.: US 6,548,091 B2
(45) Date of Patent: *Apr. 15, 2003

(54) METHOD FOR DETERMINING THE QUALITY OF CEREALS

(75) Inventor: Leif Bohlin, Sjöbo (SE)

(73) Assignee: Skanska Lanimännen Ek För, Malmo (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/311,287

(22) Filed: May 14, 1999

(65) Prior Publication Data

US 2002/0127309 A1 Sep. 12, 2002

Related U.S. Application Data (63) Continuation of application No. PCT/SE97/01922, filed on Nov. 14, 1997.

(30) Foreign Application Priority Data

Nov. 14, 1996 (SE) .............................. 9604174

(51) Int. Cl.⁷ .............................. G01N 33/10
(52) U.S. Cl. ...................... 426/231; 426/496
(58) Field of Search ................ 426/231, 549, 426/555, 618, 622, 496; 73/788, 789, 790, 791, 822, 862.09

(56) References Cited

U.S. PATENT DOCUMENTS 4,513,611 A * 4/1985 Bohlin ..................... 73/150
5,565,620 A * 10/1996 Bohlin ..................... 73/54.25

OTHER PUBLICATIONS

Faridi et al. *Dough Rheology and Baked Product Texture*, pp. 30–33, 42–47, 82–84, 343–355, Jan. 1990.*

Lebensmittelindustrie, vol. 29(1), Bohlin et al., pp. 16–18 (English Abst.), Jan. 1982.

Dialog Information Services, file 51, FSTA, Dialog Accession No. 00174775, Nowicki et al., Jan. 1978, 22(12):8–13.

File WPI, Derwent accession No. 78–E3240A, UKR Agric Mech Elec, 770921, DW7822, SU PAT 565252, Sep. 1977.

Dialog Information Services, file 51, FSTA, Dialog Accession No. 00607359 Rasper, "Proceeding from ICC '89 Symposium", pp. 265–277, Jun. 1989.

Dialog Information Services, file 51, FSTA, Dialog Accession No. 00042521, Makhmud, USSR, 1971, (1) 17–19.

Chemistry and Industry, Aug. 10, 1968, P. W. Heaps et al., pp. 1095–1096.

Derwent's Abstract, No. 58485 C/33, week 8033, Abstract of SU706773 (MOSC FOOD TECHN INST), Dec. 30, 1979.

Physical Dough Tests, AACC Method 54–40A, "Mixograph Method," First approval Apr. 13, 1961; revised Oct. 22, 1988, pp. 1–5.

Cereal Foods World, Back To The Basics, "Dough Rheological Tests[1]," C. E. Walker et al., Jan.–1996, vol. 41, No. 1, pp. 23–28.

Bakers Digest, Karl F. Finney et al., Reprinted from the Apr.–1972 issue, vol. 46, No. 2, pp. 32–35, 38–42, 77.

* cited by examiner

*Primary Examiner*—Keith Hendricks
(74) *Attorney, Agent, or Firm*—Birch, Stewart, Kolasch & Birch, LLP (57) ABSTRACT

A method for assessing the quality of cereals, comprising the steps of preparing a dough by mixing a cereal type whose quality is to be assessed, deforming the dough by mixing so that stress arises in the dough, letting the stress in the dough relax subsequent to the deformation of the dough, registering the stress in the dough during the relaxation and using the stress for assessing the quality, the mixing and the relaxing being carried out in one and the same container.

13 Claims, 6 Drawing Sheets

METHOD FOR DETERMINING THE QUALITY OF CEREALS

This application is a Continuation of Copending PCT International Application No. PCT/SE97/01922 filed on Nov. 14, 1997, which designated the United States and on which priority is claimed under 35 U.S.C. § 120, the entire contents of which are incorporated by reference.

FIELD OF THE INVENTION

The present invention relates to methods for assessing the quality of cereals.

BACKGROUND OF THE INVENTION

It is known that different qualities of wheat are required for different applications. Bread-baking, for example, requires wheat which ensures that the dough rises a great deal and that a large bread volume is obtained. On the other hand, biscuits are preferably baked from wheat which provides doughs which are not as fluffy. Pasta-making, in turn, requires wheat which provides a dough which can be extruded, while wheat which is to be used as forage should have high forage functionality, i.e. result in large growth in the animals which are being fed.

In order to optimize the use of wheat and to produce finished products which are the best possible, it is thus important for users to be able to buy wheat of the right quality. This presupposes that the quality is known. However, the fact is that different types of wheat can be of different qualities, but the same types of wheat can also be of different qualities because of, for example, different growing conditions, different weather conditions and different fertilizing. Consequently, the quality must be assessed experimentally.

In Swedish grain depots, the quality of a shipment of wheat is normally assessed by a sample being taken from the shipment and its falling number, its water content and its protein content being assessed. Payment is then based on these values. However, this method is not completely reliable, since it does not always measure the quality of the wheat. For example, it is possible to increase the protein content by increased fertilization without improving the quality in terms of baking volume or forage functionality. Consequently, the quality assessment described above is often combined with test baking. However, test baking takes such a long time that the result cannot be used at depots for sorting shipments of grain by quality.

Accordingly, there is a need for a new method for assessing cereal quality.

A known apparatus, which is used in studies of the quality of wheat, is the mixograph, which is available from TMCO, 501 Jay Street, Lincoln, Nebr., USA. The use of the mixograph is described in the AACC Standard 54-40A.

In short, the mixograph comprises a bowl, in the bottom of which three pins are fixedly placed and in the lid of which four pins are movably arranged. The mixing bowl is mounted on a vertical shaft so that it can rotate around it. An arm is fitted to the bowl. In the one end of the arm a spring is attached, which extends perpendicular to the arm and which is fixedly anchored in the base of the mixograph. A pen is attached to the other end of the arm.

The mixograph is used as follows. A sample of wheat of which the quality is to be assessed is milled into flour and is poured into the bowl of the mixograph. Water is added. The flour and the water are mixed to form a dough by the movably arranged pins being caused to rotate around the fixed pins. Subsequently, the mixing of the dough continues for a predetermined period of time. In connection with the mixing, stress arises in the dough. The stress causes a torque on the mixing bowl. The torque is registered on a sheet of paper which scrolls forward at a constant speed under the pen. The curve obtained is called a mixogram and is used as an aid for assessing the quality of the wheat. Normally, the mixogram is studied visually, in which case mixograms of different samples are compared. It is also known to correlate individual parameters which are determined from the mixogram with measures of quality, such as baking volume or dough quality. The parameters mentioned in the AACC Standard are:

Peak time, i.e. the time it takes for the torque to reach the maximum level;

The area under the curve from the beginning of the mixing to a specified point in time;

Middle peak height, i.e. the maximum height in the middle of the curve; and

The angle between the ascending and the descending parts of the curve at the maximum torque.

So far, the mixograph has only been used in laboratories, and not in depots. In order to permit its use in depots, it must be possible to carry out the quality assessment in a short period of time. This is not the case at present, since the mixograph only produces curves which then have to be evaluated. Furthermore, a high correlation is required with the cereal quality which is to be assessed. A minimum level of 80–85% has been mentioned.

Other well-known apparatus for testing the quality of doughs are the farinograph, the extensograph and the alveograph, which are described in, for instance, an article by P. W. Heaps et al. "The rheological testing of wheat glutens and doughs", p. 1095–1096 in Chemistry and Industry, Aug. 10, 1968. These apparatus are likewise unsuitable for quality assessment at depots or other commercial applications where it is a requirement that the quality assessment can be carried out simply and in a short period of time.

In the article "Relaxometrie—ein neuer Weg zur Qualitatskontrolle von Lebensmitteln" in Lebensmittel-industrie 29 (1982), the inventor of the present invention suggests that the viscous and elastic properties of semi-solid substances can be studied by means of stress relaxation. More specifically, a sample of the semi-solid substance is sheared between a cone and a plate, and a relaxing curve for the semi-solid substance is registered. The relaxing curve can be used for quality control of gluten in wheat. This known equipment is only used in laboratory tests and thus is not suitable for commercial use.

Naturally, the problems described above with respect to quality assessment of wheat also exist in the quality assessment of other cereals.

SUMMARY OF THE INVENTION

One object of the invention is thus to provide a new method, which can be used for assessing the quality of cereals.

Another object of the invention is to provide such a method and such an apparatus which can be used for quick and easy quality assessment of cereals.

A further object of the invention is to provide such a method and such an apparatus which can be used for quality assessment of cereals with a high degree of prediction.

Yet another object of the invention is to provide such a method and such an apparatus which are suitable for use in grain depots.

The above-mentioned objects are achieved by methods and apparatus which have the features stated in the appended claims.

The invention thus combines the known mixograph technique with the insight that valuable information about the quality of a cereal type can be obtained by studying how the stress in a dough, which contains the cereal in question, relaxes subsequent to the dough having been subjected to deformation. Mixing is a simple and known technique for achieving a dough and deforming the same. However, unlike in the known mixograph technique, the deformation is interrupted and the quality assessment is based on the stress in the dough when it relaxes. As a result, a very high degree of prediction can be achieved. Tests show that relaxing parameters correlate very well with the quality of cereals. For example, with three relaxing parameters a correlation of more than 88% with baking volume for wheat has been achieved.

Moreover, the fact that the deformation is effected by means of mixing and the mixing and the relaxing are effected in one and the same container, permits the quick and simple handling which is suitable for use in, for example, grain depots.

As was indicated in the introduction, the quality of a cereal type can be represented by, for example, a measure of the baking volume, a measure of the extrudability, or a measure of the forage functionality. It can also be represented by of a measure of some other quality characteristic, which correlates with one or more relaxing parameters.

The invention has been tested with very good results as regards wheat. It is presumed that it can be applied to other types of bread cereals, such as barley, rye, and oats, with equally good results. It is also presumed that the invention can be used for assessing the quality of rice, yams, cassava and other starch-based plants. Accordingly, when the term cereals is used in this application, it shall include these and similar products.

According to the invention, a dough is thus prepared by mixing the cereal type whose quality is to be assessed. When the cereal type is a grain, the dough is suitably made with flour from the cereal type and water. When the cereal type is not suitable for milling into flour, it can be worked in some other manner, e.g. it can be chopped, and liquid can be added.

The deformation of the dough, which consists of extensional strain, is preferably performed until the dough is fully developed, which it is considered to be when the stress in the dough reaches the maximum. Obviously, the deformation must continue for a short while after the maximum has been reached to make it possible to register that the maximum has been passed. The deformation can continue for about 1 minute after the maximum has been passed, since it is considered that the dough does not begin to break down until approximately this point in time.

Both the dough and the deformation of the same can be achieved by mixing in an apparatus which carries out mixing in the same manner as a mixograph.

According to the invention, the stress in the dough is registered. This can take place continuously or at selected times. If the stress cannot be measured directly, another quantity, which gives a measure of the stress, can be registered.

Furthermore, at least one relaxing parameter is suitably determined on the basis of the stress registered during the relaxing and is used in a predetermined calculation model. Since the relaxing parameter is to be used in a calculation model, a numerical value is determined for this parameter. The calculation model can preferably be a neural network which has been trained to perform the desired quality assessment for the cereal type in question. It can also consist of a linear relation which has been determined by means of, for example, multivariate analysis. A neural network can be expected to provide a somewhat higher degree of correlation since it can identify non-linear relations.

In a preferred embodiment, one lets the dough stand for a predetermined length of time subsequent to the interruption of the deformation. Subsequently, the dough is again deformed before the dough is allowed to relax. The deformation after the standing is preferably effected in such a way that the stress reaches a predetermined value, which can suitably be the value of the stress when the deformation was interrupted, i.e. close to the maximum stress. The advantage of letting the dough stand after the initial deformation is that this gives the dough time to "heal" from some of the damage it receives during the deformation. This is assumed to lead to more certain results in the quality assessment. Alternatively, the relaxation measuring can be performed immediately after the first deformation has been interrupted.

The most certain correlation with the quality is obtained if the deformation, the relaxing, and the registration of the stress are repeated several times, and an average is established of the stresses registered as a function of time, the relaxing parameter being determined on the basis of the average relaxing curve. This possibility presents an advantage compared with the traditional mixing which can only be performed once.

It has been found that the following parameters are particularly suitable for assessing the quality of cereals. The absolute stress in the dough at a predetermined time subsequent to the interruption of the deformation, the relative stress in the dough, i.e. the absolute stress at a predetermined time subsequent to the interruption of the deformation divided by the maximum stress, the maximum on a curve of the derivative of the relative stress as a function of the logarithm of time divided by the value of the relative stress at this point, and the slope of the curve of the derivative of the relative stress as a function of the logarithm of time in the final phase of the relaxing. In a multivariate analysis some of the parameters must be inverted.

The very highest degree of correlation with cereal quality has been obtained when the assessment of the quality has been based on one or more relaxing parameters in combination with one or more mixing parameters, i.e. parameters which are determined on the basis of the stress registered during the deformation. In such cases, a correlation of more than 92% with baking volume for wheat has been achieved.

A mixing parameter which has been found to be particularly useful is the so-called build-up parameter, which is determined as the difference between the maximum stress in the dough during the deformation and the stress in the dough at the point in time when all the liquid has been absorbed. This is an entirely new parameter which alone has a correlation of more than 80% with baking volume for wheat. It is presumed that it also has a high correlation with measures of quality for other cereal types. Since this parameter has such a high degree of correlation, it alone could be used for assessing quality. Accordingly, in this case, one would not need to effect any relaxing, but rather a traditional mixogram could be recorded, the build-up parameter be determined with the aid of a calculation unit and be used for quality assessment, e.g. in a predetermined calculation model. The advantage of this would be that no advanced calculation equipment would be needed. The build-up parameter can, of course, also be combined with other mixing parameters for improved correlation with cereal quality.

An apparatus for assessing quality based on relaxation contains means for preparing a dough by mixing a cereal type whose quality is to be assessed and for deforming the dough by mixing so that stress arises in the dough, as well as means for registering the stress in the dough. In addition, the apparatus has a calculation unit, which is adapted to assess the quality of said cereal type with the aid of the stress in the dough which has been registered during the relaxing of the dough subsequent to its deformation, the apparatus comprising a container in which both the mixing and the relaxing are effected.

In a preferred embodiment, the calculation unit determines a relaxing parameter on the basis of the stress registered during the relaxing and uses this relaxing parameter in a predetermined calculation model for assessing the quality.

Essentially the same apparatus as the one described above can be used for quality assessment based on the above-mentioned build-up parameter. However, in this case, no relaxing is performed, but instead the calculation unit calculates a mixing parameter by determining the difference between the maximum for the stress in the dough during mixing and the stress in the dough when all the water has been absorbed. This mixing parameter is used in the quality assessment.

Unlike the output signal from the known mixograph, the output signal from this apparatus is a direct measure, preferably a numerical value, of the quality of the cereal type examined. Accordingly, this apparatus is suitable for commercial use. It is easy to operate, since the process can be made completely automated. The user only needs to pour in suitable amounts of the cereal type which is to be quality assessed and of liquid.

In order to achieve the dough and the deformation of the same, the principle of the mixograph is preferably used, i.e. a container and a plurality of deformation members which deform different parts of the dough in different directions. The advantage of this is, inter alia, that the mixograph is a known apparatus which is available on the market.

By the methods and the apparatus according to the invention, the quality of different cereals types can be predicted with high accuracy by a simple and quick procedure. The invention can advantageously be used in depots, in which case a fairer price can be obtained for the farmers who have grown the cereals. Moreover, the invention makes it possible to bring out new qualities in cereals which are specially adapted to particular applications. The invention can advantageously also be used in bakeries, in the processing industry, in mills and like places where cereal quality needs to be assessed.

BRIEF DESCRIPTION OF THE DRAWINGS

The invention will be described in more detail below by way of embodiments with reference to the accompanying drawings, in which.

DESCRIPTION OF PREFERRED EMBODIMENTS OF THE INVENTION

Figure 1:
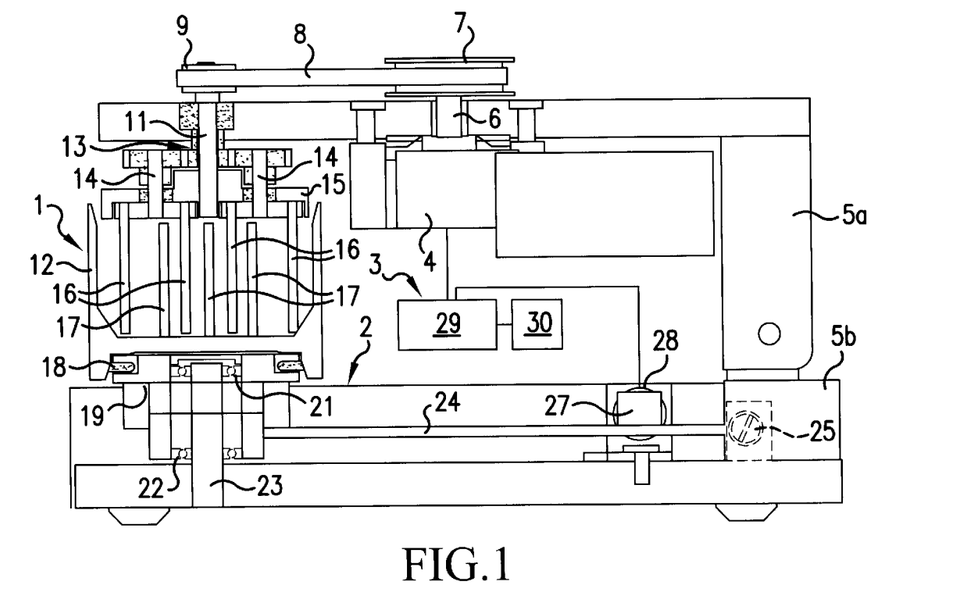
FIG. 1 is a schematic cross-sectional view of an apparatus according to the invention.

FIG. 1 shows how an apparatus according to the invention can be realized. The apparatus shown in FIG. 1 essentially comprises means 1 for preparing and deforming the dough, means 2 for measuring torque on the mixing bowl, and a calculation unit 3.

The means 1 for preparing and deforming the dough comprise a motor 4, which is suspended from a cantilever beam 5a, which is articulated to the base 5b of the apparatus. The motor 4 has an output shaft 6 to which a first pulley 7 is fitted. The first pulley 7 is connected by the intermediary of a belt 8 to a second pulley 9, which is fitted to a drive shaft 11. A planetary gear 13 is attached to the drive shaft 11. By the intermediary of the planetary gear 13, the first drive shaft 11 drives a second and a third drive shaft 14, which extend through a cover 15 down into a mixing bowl 12 and which are each connected to two movably arranged stirring rods 16 which extend down into the mixing bowl 12. Since the cantilever beam 5a is articulated to the base 5b, the cover 15 with the stirring rods 16 can be lifted off the mixing bowl 12 if necessary. Three fixed rods 17 are attached to the bottom of the mixing bowl 12 which extend upwards in the mixing bowl 12 and around which the movable stirring rods 16 rotate. The mixing bowl 12 is fastened with a bayonet catch 18 in a housing 19 which, with the aid of an upper and a lower ball bearing 21 and 22 respectively, is mounted on a pivot pin 23 which is attached to the base 5b. The mixing bowl 12 is thus free to rotate around the pivot pin 23.

The means 2 for measuring the torque comprise an arm 24, which is connected to and extends horizontally from the housing 19. The end 25 of the arm facing away from the housing 19 is attached between two springs 26 which extend perpendicular to the arm, each in one direction in the horizontal plane. The springs are attached to the base 5b. A tin plate 27 is fitted to the arm 24 a short distance from the springs 26. Opposite the tin plate 27, perpendicularly to the plane of the paper in FIG. 1, an inductive transducer 28 is fitted to the base. The arm 24 prevents the mixing bowl 12 from rotating.

The inductive transducer 28 and the motor 4 are connected to an intelligent control and registration unit 29, which in turn is connected to a personal computer 30, which determines the quality on the basis of the stresses measured. The calculation model used is stored in the personal computer. The control and registration unit 29 and the personal computer 30 jointly form the calculation unit 3.

Figure 2:
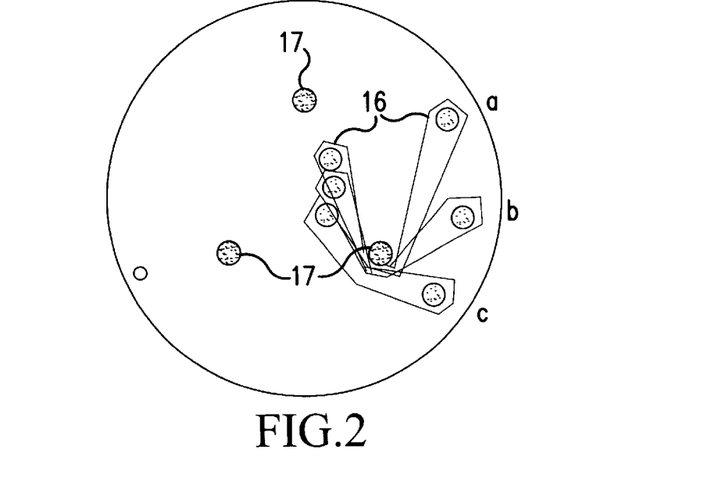
FIG. 2 is a schematic view showing the deformation of a dough with the aid of an apparatus according to the invention.

The apparatus functions as follows. The motor 4 drives the first drive shaft 11 at about 88 rpm. Thereby, the movable stirring rods 16 will rotate around the second and the third drive shaft 14 and simultaneously around the first drive shaft 11. The dough will then be deformed, as illustrated in FIG. 2, which schematically shows the mixing bowl 12 seen from above, the three fixed rods 17 and two of the movable stirring rods 16 in three different positions a, b, and c. When the dough in the mixing bowl is being deformed, the mixing bowl will be acted upon by a torque, which reflects the stress in the dough. However, the arm 24 substantially prevents the mixing bowl 12 from rotating. The torque is absorbed by the arm 24 which depending upon the size of the torque turns through a small angle horizontally. In connection with this turning, the distance to the inductive transducer 28 changes, whose output signal is a measure of the distance to the tin plate 27, which in turn thus is a measure of the torque. The transducer 28 is coupled to the control and registration unit 29, which controls the motor and registers the torque measured by the transducer.

Figure 3:
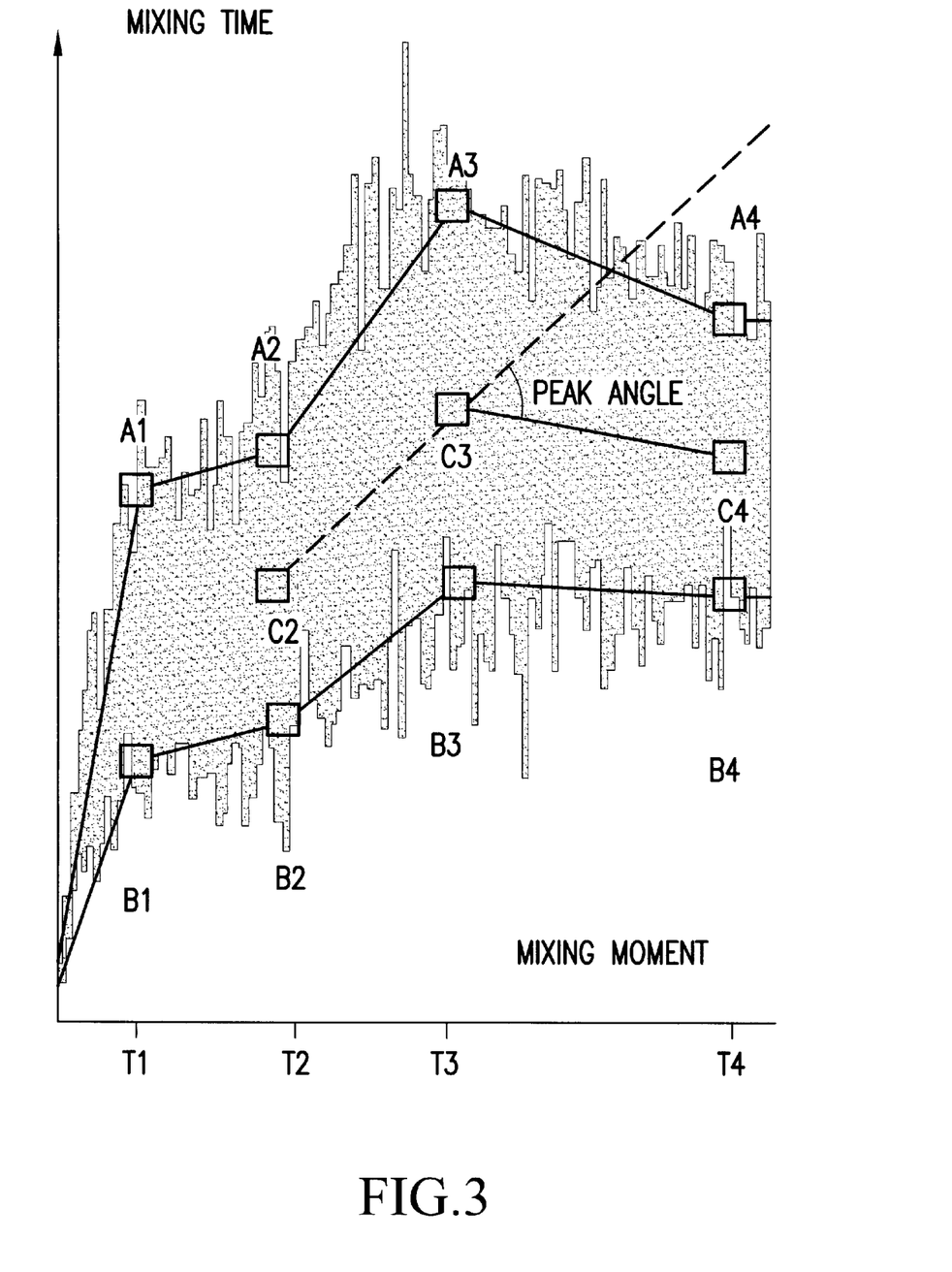
FIG. 3 is a graph showing stress as a function of time in the deformation of a dough.

The method according to the invention is preferably carried out as follows when the quality of wheat is to be assessed. A sample of the wheat is milled into flour. The flour is placed in the mixing bowl 12. Water is added. The motor 4 is started and the flour and the water are blended into a dough. Subsequently, the mixing in the mixing bowl continues. During the whole mixing process the variations in the torque as a function of time are registered with the aid of the inductive transducer 28. The mixing continues until the maximum of the torque has been registered and a further 30 s thereafter. FIG. 3 shows a curve of the torque as a function of time for a wheat dough which has been mixed in an apparatus as described above.

When the mixing has been interrupted, the dough is allowed to stand for a predetermined period of time. When the standing period is over, the computer commands the motor to turn the first drive shaft so that substantially the same torque arises on the mixing bowl as was measured when the mixing was interrupted. Subsequently, the dough is allowed to relax and the torque on the mixing bowl during the relaxing is registered. The turning and the subsequent relaxing are effected five times.

Figure 4:
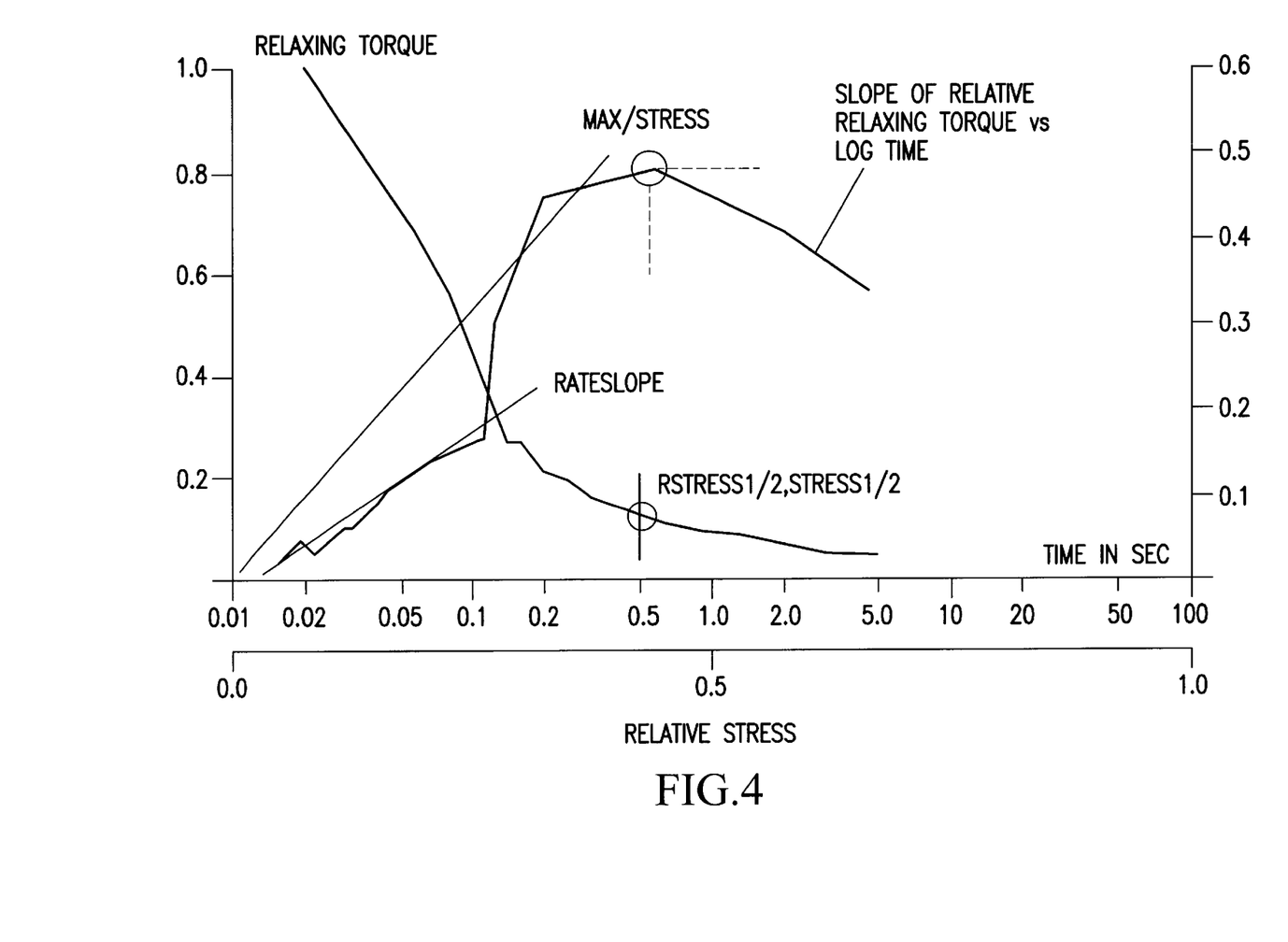
FIG. 4 is a graph showing how different relaxing parameters are determined.

Next, the information registered in the computer during the mixing and the relaxing is processed as follows. First, the computer 30 averages the five relaxing curves which show the torque as a function of time during the relaxing. Subsequently, the relaxing torque as a function of the logarithm of time as well as the slope, i.e. the derivative, of the relaxing torque curve as a function of the logarithm of time are plotted. FIG. 4 shows a graph of these two curves for a wheat sample which has been mixed and been allowed to relax in an apparatus as described above.

From the plotted curves, the following four relaxing parameters are determined:

1) The absolute torque 0.5 s subsequent to the interruption of the mixing ("stress½"), 2) the relative torque, i.e. the absolute torque 0.5 s subsequent to the interruption of the deformation divided by the maximum torque, ("rstress½"), 3) the maximum value on a curve of the derivative of the relative torque as a function of the logarithm of time ("max/stress") divided by the relative torque for this point, and 4) the slope value for the curve of the derivative of the relative torque as a function of the logarithm of time in the final phase of the relaxing, i.e. at low values of the relative torque ("rateslope").

In addition, five parameters are determined from the traditional mixogram showing the torque as a function of time during the mixing. In the mixogram in FIG. 3 are indicated a number of break points A1–A4; B1–B4; C2–C4 and T1–T4 which are used in determining parameters. A1 denotes the maximum mixing moment approximately when the first mixing-in of water has taken place, A2 denotes the maximum mixing moment approximately when all the water has been absorbed, A3 denotes the peak value of the maximum mixing moment during the deformation, i.e. the point where the dough is optimally developed and A4 denotes the maximum mixing moment after a further about 30 s of mixing at the point where the actual breakdown of the dough begins. B1–B4 and C1–C4 are the corresponding points for the minimum mixing moment and the average mixing moment, respectively, and T1–T4 are the corresponding points in time. The five parameters are the build-up parameter, which is determined as A3–A2 in FIG. 3, the area below the curve ("areabelow"), which is determined as the area below the curve which is defined by the points B1–B4, the initial build-up, which is determined as A2–A1, the maximum center ("maxcenter"), which is determined as (A3+B3)/2 and maximum time ("maxtime"), which is defined by T3. In this context, it should be noted that the build-up parameter could also be determined as A3–A1 and that the exact placement of points A1–A3 can vary somewhat.

The nine parameters determined in this manner are fed as input signals to a neural network which has been trained to determine baking volume on the basis of these nine parameters. The output signal from the neural network gives a measure of the baking volume which will be obtained when baking with this sample of wheat.

EXAMPLES

Samples were taken from 95 different sorts of autumn wheat, which had been grown in different locations by different growers. These autumn wheats constituted a typical cross-section of the autumn wheats which had been grown in an area of southern Sweden.

The samples were analysed to determine their protein content and water content. Subsequently, the samples were milled into flour and test-baked by Svenska Cereallaboratoriet AB, Svalov, Sweden according to a standardised baking method.

For each sample, 25 g of flour was poured into the mixing bowl in the above-mentioned apparatus. Water was added according to the modified AACC Standard for Swedish wheats. Subsequently, the dough was mixed and was allowed to relax in the manner described above. From the torque curves which were registered during the mixing and the relaxing, the above-mentioned nine parameters were determined, which were analyzed using multivariate analysis, the following results being obtained.

Analysis of the Mixing Parameters Only

In this analysis, the following parameters were used as X variables: the build-up parameter, the area below the curve, initial build-up, maximum center and maximum time. Bread volume was used as the Y variable. In the analysis, the number of parameters was reduced beginning at the end of the above list. The following results were obtained:

| Model | Correlation with Bread Volume |
| --- | --- |
| 5 variables, 2 factors | 82,9% |
| 4 variables, 2 factors | 83,3% |
| 3 variables, 2 factors | 83,5% |
| 2 variables, 2 factors | 83,4% |
| 1 variables, 1 factor | 80,4% |

Figure 5A:
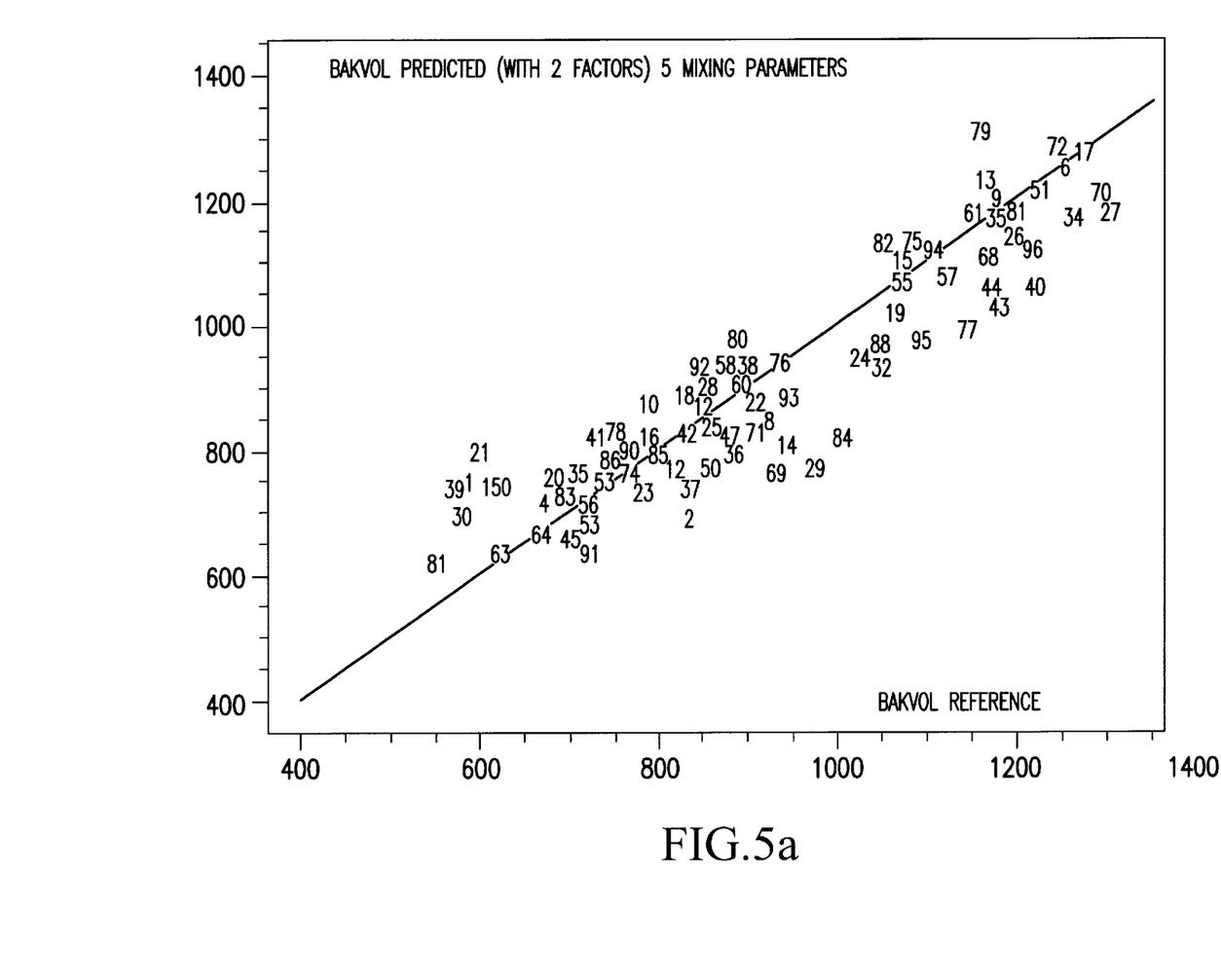
FIGS. 5a–c are graphs showing the correlation between different parameters and bread volume.

Thus, with the aid of three parameters, a degree of prediction of 83, 5% was obtained. In this case, the build-up parameter alone provided a degree of prediction of over 80%. FIG. 5a shows a graph of the predicted baking volume as a function of the actual baking volume obtained.

Analysis of Relaxing Parameters Only:

In this analysis the following three parameters were used as X variables: stress½, stress/max, and 1/rateslope. Bread volume was used as the Y variable.

Figure 5B:
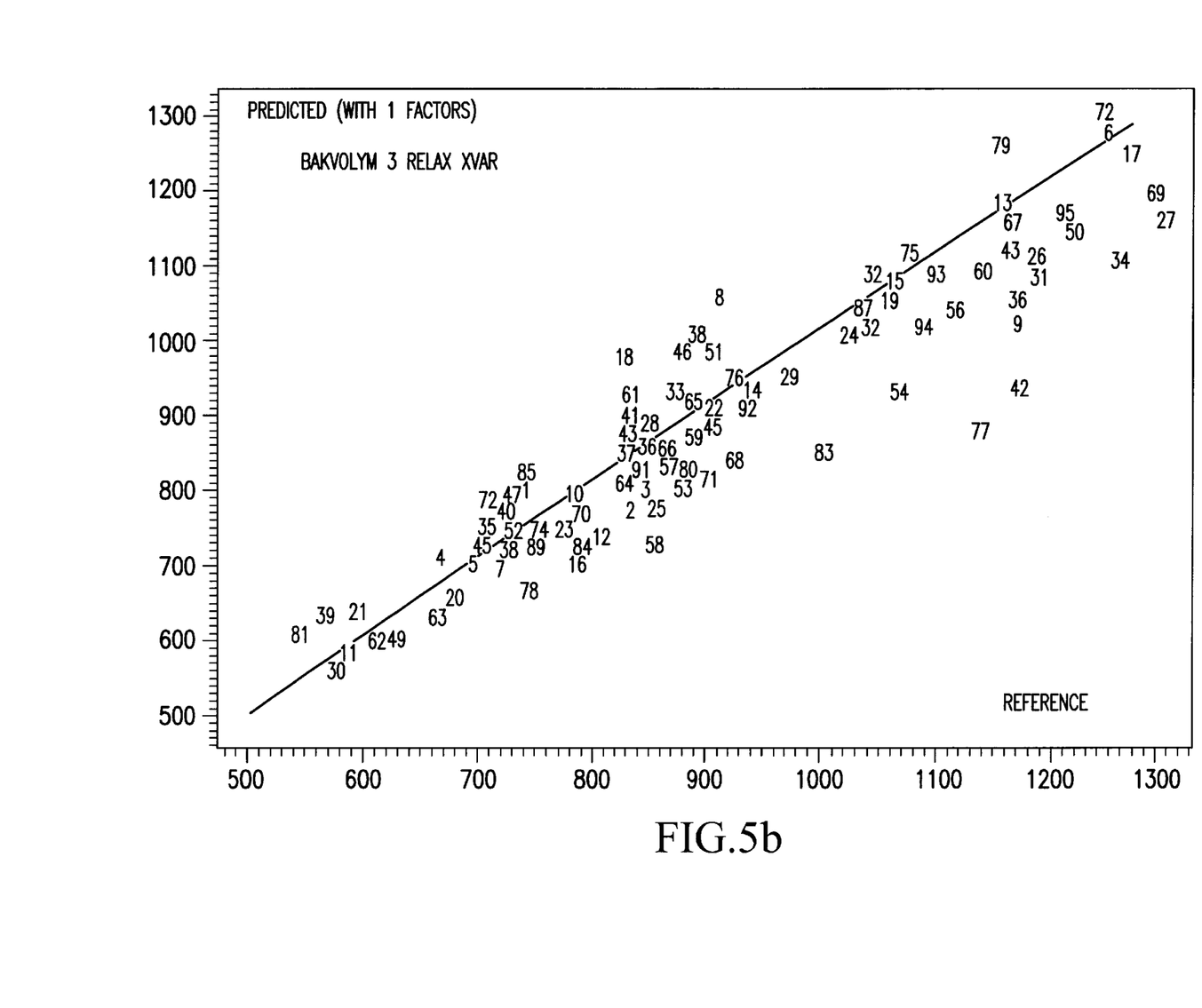

With the aid of these three parameters and two factors, a degree of prediction of 88.4% was obtained. FIG. 5b shows a graph of the predicted baking volume as a function of the actual baking volume obtained in this case.

Analysis of Mixing Parameters and Relaxing Parameters:

In this analysis, the five mixing parameters as well as the three relaxing parameters were used as X variables and baking volume was used as the Y variable.

Figure 5C:
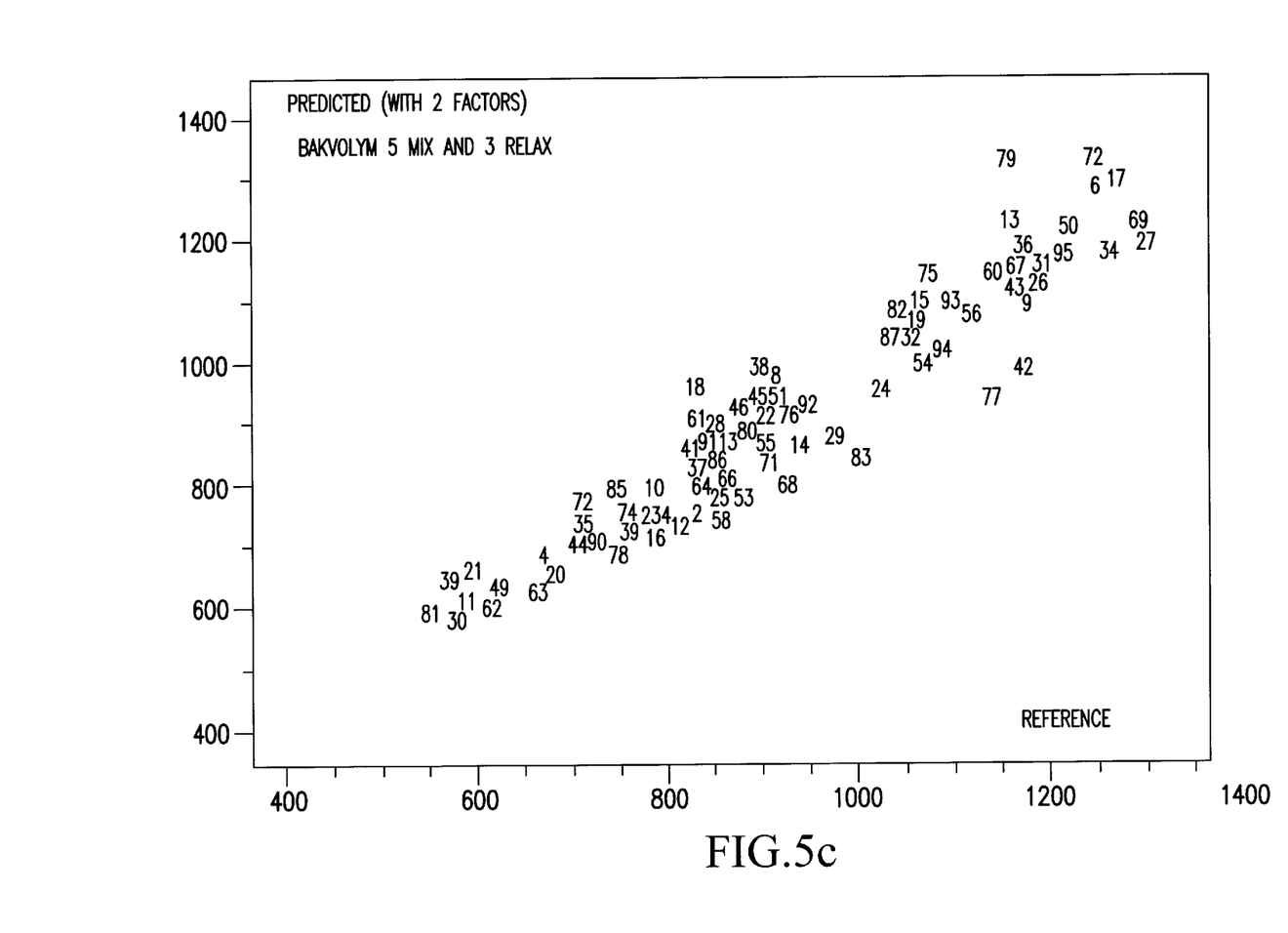

With the aid of these eight variables and three factors, a degree of prediction of 92.3% was obtained. FIG. 5c shows a graph of the predicted baking volume as a function of the actual baking volume obtained in this case.

As can be seen from the above, the use of three relaxing parameters provides a higher correlation with baking volume than the use of three mixing parameters, and the use of both relaxing parameters and mixing parameters provides an even higher correlation.

In the above description, parameters are stated which are suitable for use in the assessment of bread volume for wheat. It is presumed that these parameters are also suitable in assessing the quality of other cereal types and in assessing measures of quality other than baking volume. However, if the invention is to be used for applications other than the one described above, suitable parameters as well as the correlation between these and the measure of quality in question can be determined by means of multivariate analysis, which is a recognised method of analysis. As an alternative, a neural network can be trained in a suitable manner.

The Build-up Parameter

The way in which quality assessment is carried out by the use of relaxation has been described above. The same apparatus and the same procedure as described above can, of course, be used if one wishes to carry out quality assessment with the aid of the build-up parameter only or with the aid of the build-up parameter in combination with other mixing parameters. Naturally, in this case, the actual relaxing does not need to be performed.

What is claimed is:

1. A method of analyzing a cereal for determination of one measure from the group consisting of a measure of baking volume of a dough of said cereal, a measure of extrudability of a dough made from said cereal and a measure of forage functionality of said cereal; comprising the steps of:
   preparing a dough by mixing an amount of said cereal with a liquid;
   deforming the dough by mixing the thus-prepared dough in a container so that stress arises in the dough, said stress causing a torque on the container;
   recording the torque in a calculation unit during deformation of the dough;
   determining, in the calculation unit, that a maximum of the recorded torque has been passed;
   interrupting the mixing when the calculation unit has determined that the maximum of the recorded torque has been passed, the interruption of the mixing causing the stress in the dough to relax in said container;
   continuing to record in the calculation unit the torque on the container during the relaxation of the dough, which occurs when the dough is interrupted; and
   using the torque recorded during the relaxation of the dough for providing an input signal to a predetermined calculation model in the calculation unit;
   calculating, with the aid of the predetermined calculation model in the calculation unit, a numerical value which constitutes said one measure,
   wherein said calculation model calculates said one measure according to a predetermined linear or non-linear relation between said input signal and said one measure.

2. The method according to claim 1, wherein the calculating step comprises calculating, in the calculation unit and using the torque recorded during the relaxation of the dough, at least one relaxing parameter, and inputting said at least one relaxing parameter as the input signal to the predetermined calculation model.

3. The method according to claim 1, wherein the step of interrupting the mixing is performed prior to the dough breaking down.

4. The method according to claim 1, further comprising the steps of:
   letting the dough stand for a predetermined period of time after the mixing has been interrupted;
   restarting the mixing;
   determining, in the calculation unit, that said maximum of the recorded torque has been reached; and
   interrupting the mixing when the calculation unit has determined that the torque has reached said maximum of the recorded torque.

5. The method according to claim 2, wherein the steps of deforming, recording, interrupting and continuing to record the torque during relaxation of the dough are repeated several times, and further comprising the step of calculating, in the calculation unit, the average as a function of time of the torque recorded during the relaxation of the dough as a function of time for the repeated relaxations, and wherein the calculation of said at least one relaxing parameter is based on said average.

6. The method according to claim 2, wherein each of said at least one relaxing parameter is a parameter from the group consisting of the absolute torque at a predetermined time subsequent to the interruption of the mixing, the relative torque which is the absolute torque at a predetermined time subsequent to the interruption of the mixing divided by the maximum torque, the maximum on a curve of the derivative of the relative torque as a function of the logarithm of time divided by the relative torque at this point, and the slope of the curve of the derivative of the relative torque as a function of the logarithm of time in the final phase of the relaxing.

7. The method according to claim 1, wherein the predetermined calculation model consists of a neural network, which has been trained to calculate said one measure.

8. The method according to claim 2, wherein the calculating step further comprises calculating in the calculation unit and on the basis of the torque recorded during the deformation of the dough, at least one mixing parameter, and inputting said at least one mixing parameter as an input signal to the predetermined calculation model.

9. The method according to claim 8, wherein said mixing parameter is calculated on the basis of the difference between the maximum of the recorded torque and the recorded torque when all the liquid has been absorbed.

10. The method according to claim 1, wherein said cereal is wheat.

11. A method of analyzing a cereal for determination of one measure from the group consisting of a measure of baking volume of a dough of said cereal, a measure of extrudability of a dough made from said cereal and a measure of forage functionality of said cereal; comprising the steps of:

preparing a dough by mixing an amount of said cereal with a liquid;

deforming the dough by mixing the thus-prepared dough in a container so that stress arises in the dough, said stress causing a torque on the container;

recording the torque in a calculation unit during deformation of the dough;

determining in the calculation unit a first value of the torque, which corresponds to the maximum of the torque recorded during deformation;

determining in the calculation unit a second value of the torque, which is the value of the torque when all liquid in the dough is absorbed;

calculating a mixing parameter which is the difference between the first and second values; and using the mixing parameter for providing an input signal to a predetermined calculation model in the calculation unit;

calculating, with the aid of the predetermined calculation model in the calculation unit, a numerical value which constitutes said one measure, wherein said calculation model calculates said one measure according to a predetermined linear or non-linear relation between said input signal and said one measure.

12. The method according to claim 11, wherein said predetermined calculation model consists of a neural network.

13. The method according to claim 11, wherein said cereal is wheat.

* * * * *